United States Patent [19]

Bruso

[11] Patent Number: 4,576,795
[45] Date of Patent: Mar. 18, 1986

[54] DISPOSABLE STERILIZER VACUUM TEST PACK

[75] Inventor: Loran H. Bruso, Ontario, Calif.

[73] Assignee: Warner-Lambert Company, Morris Plains, N.J.

[21] Appl. No.: 605,084

[22] Filed: Apr. 30, 1984

Related U.S. Application Data

[63] Continuation-in-part of Ser. No. 536,798, Sep. 28, 1983.

[51] Int. Cl.⁴ ............................................. G01N 21/78
[52] U.S. Cl. ..................................... 422/58; 53/447; 422/61; 436/1
[58] Field of Search ............... 436/1; 422/55–57, 422/61, 86–88, 26

[56] References Cited

U.S. PATENT DOCUMENTS

| 2,249,867 | 1/1938 | Snelling | 422/56 |
| 2,250,980 | 7/1941 | Workman et al. | 422/56 |
| 3,386,807 | 6/1968 | Edenbaum | 436/1 |
| 3,523,011 | 5/1968 | Bhiwandker et al. | 422/57 |
| 4,087,332 | 5/1978 | Hansen | 422/56 |
| 4,145,180 | 3/1979 | Anderson | 422/86 |
| 4,195,058 | 3/1980 | Patel | 422/56 |
| 4,382,063 | 5/1983 | Romito et al. | 422/57 |
| 4,410,493 | 10/1983 | Joslyn | 422/56 |
| 4,448,548 | 5/1984 | Foley | 422/58 |
| 4,486,387 | 12/1984 | August | 422/57 |

OTHER PUBLICATIONS

Bowie et al.; *The Lancet;* Mar. 16, 1963; pp. 586–587.

Primary Examiner—Barry S. Richman
Assistant Examiner—C. M. Delahunty
Attorney, Agent, or Firm—Neil K. Nydegger

[57] ABSTRACT

An improved test pack for determining the efficiency of a vacuum in an autoclave comprises a porous bundle partially including open cell foam and having a plurality of non-porous gas impermeable layers placed on its surface to leave a portion thereof exposed. A sheet with a steam sensitive indicator ink printed thereon is embedded in the bundle for placement in an autoclave where a vacuum is drawn to evacuate air therefrom through the exposed surface portions of the bundle. Steam is then introduced to replace the evacuated air and react with the indicator ink wherever there is contact. The amount of indicator ink contacted by the steam is a measure of the efficiency of the vacuum.

8 Claims, 7 Drawing Figures

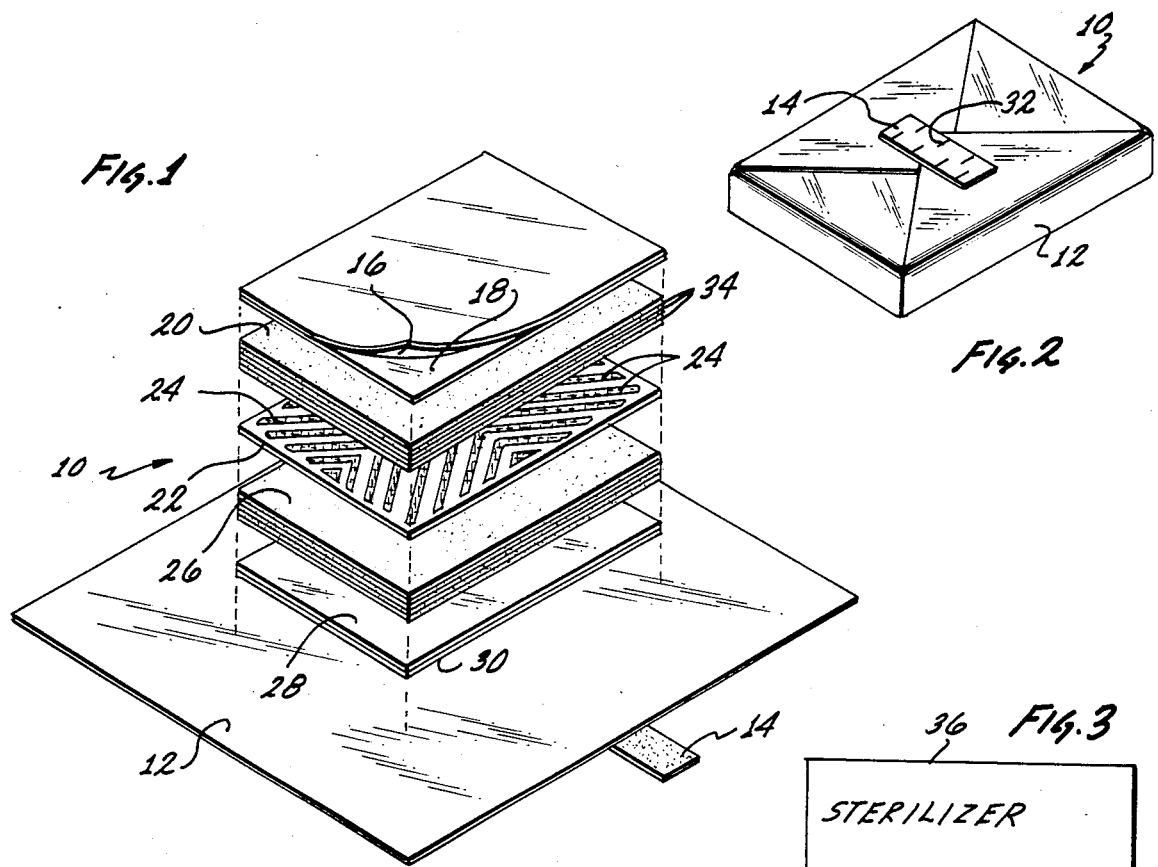
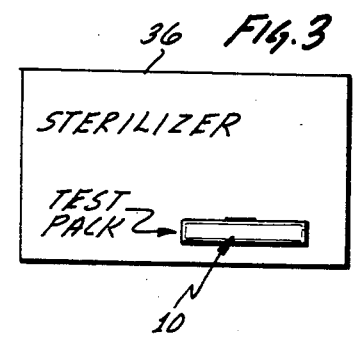
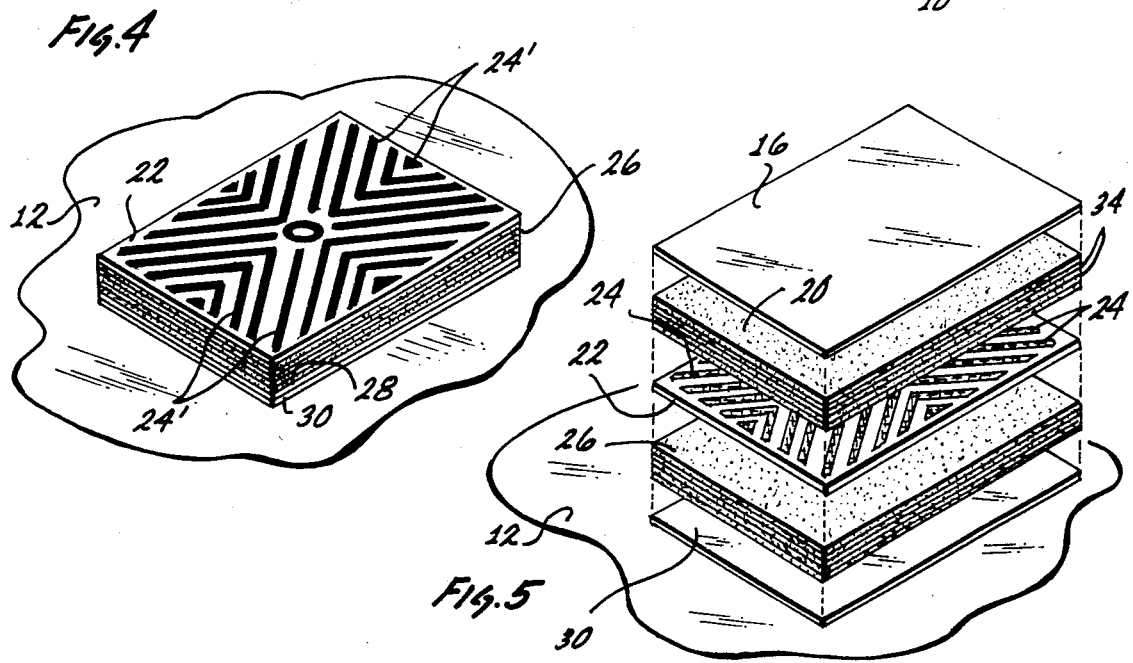

DISPOSABLE STERILIZER VACUUM TEST PACK

BACKGROUND OF THE INVENTION

This application is a continuation-in-part of my prior application for a "Disposable Sterilizer Vacuum Test Pack," Ser. No. 536,798 filed Sept. 28, 1983.

This invention relates generally to a device for testing the efficiency of a created vacuum. More specifically, the invention relates to a disposable test pack for use in determining the efficiency of the vacuum drawn in a steam sterilizing unit. The present invention is particularly, though not exclusively, useful in the testing of steam sterilizing equipment, such as an autoclave, used in the sterilization of hospital and medical equipment.

DESCRIPTION OF THE PRIOR ART

Well known in the pertinent art are several devices which indicate when sterilizing conditions have been achieved. Typically, such devices are indicator inks which are printed on a substrate and placed in the environment with the articles to be sterilized. Changes in the color of the inks show when effective sterilizing conditions have been achieved. Despite the efficacy of such indicators, they are effective only for the conditions to which they are exposed. Thus, unless the indicator can be placed directly into the particular area to be sterilized, there can be no real assurance that sterilizing conditions were achieved. This is a particularly troublesome problem where porous, permeable, holey or compartmentalized articles are concerned. Where such articles are concerned, there is a need to determine, with some degree of certainty, whether sterilizing conditions are achievable throughout the environment in which the articles are to be placed for sterilization. For example, in a hospital environment, it is frequently necessary to sterilize bundles, containers, packages or kits which have hard to reach areas where it is difficult or impossible to place a sterilization indicator. In such cases, there is a real need for assurance that the sterilizing medium has penetrated and been effective in these hard to reach areas.

When steam is used as the sterilizing medium, it has been the practice to place the articles in the chamber of an autoclave device. After a vacuum is drawn in the autoclave chamber, steam is introduced into the chamber as a sterilizing medium. In such devices it is particularly important that the efficiency of the vacuum system be determined because without an effective vacuum, air can be remain entrapped in the hard to reach areas of articles and implements in the chamber. When steam is subsequently introduced into the chamber, the entrapped air forms bubbles which prevent the steam from being drawn into contact with those areas of the articles or implements where the air bubbles are located.

The industry standard for determining whether a particular autoclave system has been effective is the test commonly known as the Bowie-Dick test. In conducting this test, it has been the practice to wrap a steam sensitive indicator sheet in numerous towels and subject this package to the vacuum system and steam sterilizing cycle of the autoclave. This procedure is time consuming and laborious. Further, the efficiency of each test pack may vary depending on the porosity of the towels and the manner in which they are used to constitute the pack.

In order to overcome the labor involved in constituting a pack of the type previously described and to provide more dependable and predictable reliability, it has been proposed that porous papers be used in lieu of towels. One example of such a device is presently being marketed by the Propper Manufacturing Company Inc. under the brand name Once-A-Day ®. Such a ready-made pack obviates the need for assembly and thereby reduces the amount of labor necessary to perform the test. Although such packs have less bulk than the aforementioned towel packs, there is still a need for an even smaller more compact test pack.

In addition to the need for a smaller test pack, there is the need for a test pack which affords a consistently high degree of assurance that sterilization conditions have been achieved. This assurance can be enhanced by providing a pack which presents a more challenging and rigorous test for the vacuum system of an autoclave. When only porous materials are used to constitute the test pack, the pack's entire surface is exposed and a more rigorous test is obtained only by building up the porous layer which surrounds the steam sensitive indicator sheet. On the other hand, as envisioned by the present invention, nonporous layers can be placed on the pack to reduce the surface area of exposed porous material. Such placement of nonporous layers establishes a more challenging test for the evacuation of air and introduction of steam by altering the gas permeable passageways of the test pack. Further, use of nonporous layers permits reduced dimensions for the test pack. While the above cited advantages of using nonporous layers are significant for increasing the sensitivity of the test pack, it is still important that air and steam be able to circulate within the confined gas permeable passageways created in the test pack. Indeed, it is possible to make the test pack too sensitive. Therefore, the sensitivity of the test pack can be adjusted by the addition of materials having increased porosity. It is envisioned in the present invention that a portion of the test pack may comprise an open celled foam to control the degree of circulation of air and steam within the test pack. In light of the above, an ideal vacuum test pack is one that is easily manufactured and does not take up excessive storage space. Additionally, the test pack should be easily used, consistently reliable, and inexpensive.

Accordingly, it is an object of the present invention to provide an inexpensive, easily stored, small, cost effective test pack. It is yet another object of the present invention to provide a disposable vacuum test pack which is easily handled and which gives a reliable indication of the efficiency of the vacuum system.

SUMMARY OF THE INVENTION

A preferred embodiment of the novel improved vacuum test pack of the present invention includes a sheet having a steam discolorable indicator ink deposited thereon which is interposed between two porous pads having surfaces and edges as shown in FIGS. 6 and 7. As best seen in FIG. 6, a foam layer is associated with at least one of the porous pads to place at least a portion of the porous pad between the sheet and the foam layer. Disposed on the surfaces of the porous pads and foam layers which are exposed are nonporous layers which are preferably a plastic laminate. In an alternate embodiment a porous foam layer can be placed between each of the porous pads and the respective nonporous layer. In all embodiments a test pack bundle having a top surface and a bottom surface and an edge therebetween is formed that leaves the edge portion of each porous pad and foam layer exposed for evacuation of air therefrom and subsequent replacement with sterilizing steam. The extent to which steam penetrates the pack can be determined by subsequent inspection of the sheet and used as a measure of the efficiency of the vacuum cycle of an autoclave. The entire pack can be covered with a CSR overwrap material and held together with a tape having an indicator ink imprinted thereon to show which packs have been subjected to a sterilization process.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 1 is an exploded perspective view of the contents of the vacuum test pack;

FIG. 2 is a perspective view of the vacuum test pack folded and ready for use in an autoclave device;

FIG. 3 is a schematic representation of the test pack in a sterilizer;

FIG. 4 is a perspective view of a portion of the test pack;

FIG. 5 is an exploded perspective view of an alternate embodiment of the test pack;

DESCRIPTION OF THE PREFERRED EMBODIMENT

Figure 6:
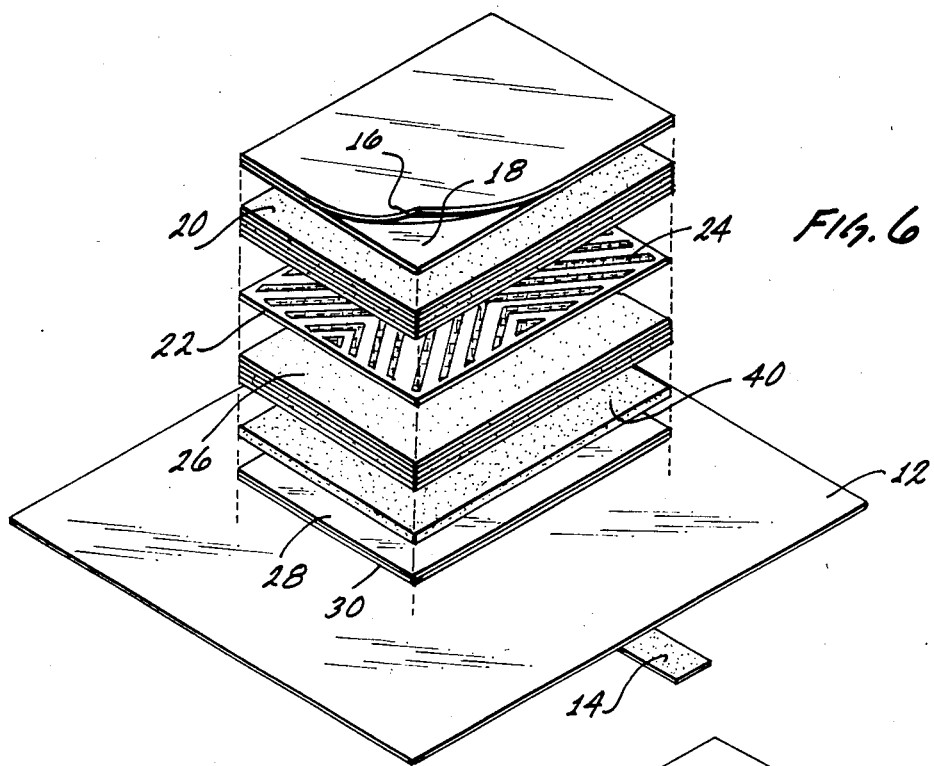
FIG. 6 is an exploded perspective view of the contents of the vacuum test pack incorporating a single foam layer.

Referring initially to FIG. 2, the vacuum test pack generally designated 10 is shown with the overwrap 12 in place and the autoclave indicator tape 14 securing the overwrap 12.

Disposed on the indicator tape 14 is a steam sensitive indicator ink 32 well known in the art which will indicate when the tape 14 and the vacuum test pack 10 have been exposed to a steam sterilization process.

In FIG. 6 the contents of the preferred embodiment of the vacuum test pack 10 are shown in an exploded perspective. Initially, it should be appreciated that an indicator sheet 22 is imprinted with an indicator ink 24 which will indicate the presence of a steam sterilization medium. As shown in FIGS. 1 and 6, the indicator ink 24 has not been exposed to a sterilization cycle. For comparison purposes, the indicator ink 24 on sheet 22 is shown in FIG. 4 as it would appear after exposure to a sterilization process. An indicator ink 24 such as the type described in the Berman patent, U.S. Pat. No. 2,118,144 which is discolorable in the presence of steam is preferable. For purposes of this invention, any porous material well known in the art, such as a blotter paper, on which ink can be deposited, may be used for the indicator sheet 22.

As shown in FIG. 6, the indicator sheet 22 is placed with a porous pad 20 disposed on one side of the indicator sheet 22 and a porous pad 26 disposed on the opposite side of the indicator sheet 22. Both porous pad 20 and porous pad 26 can be made from any porous material well known in the art. Further, the porous pads 20 and 26 can comprise a combination of various materials of differing porosity. In the preferred embodiment, porous pads 20 and 26 are formed as a stack of five 0.02" thick blotter papers of which blotter paper 34 is representative. It should be emphasized, however, that more or fewer blotter papers 34 of varying thicknesses can be used depending upon the particular needs of the device. Also, the dimensions of the pack 10 can be varied according to the number and thicknesses of blotter papers 34 needed to achieve a desired porosity value.

In the preferred embodiment, a foam layer 40 is placed in position to cover the side of porous pad 26 that is opposite from the indicator sheet 22. Foam layer 40 can be made of any open cell reticulated foam that can withstand steam sterilization. For purposes of the present invention, either an open cell polyester foam or an open cell polyurethane foam are suitable for foam layer 40. However, as will be appreciated by those skilled in the art, any open cell reticulated foam which permits circulation of air and steam over the surface of porous pad 26 will suffice.

Figure 7:
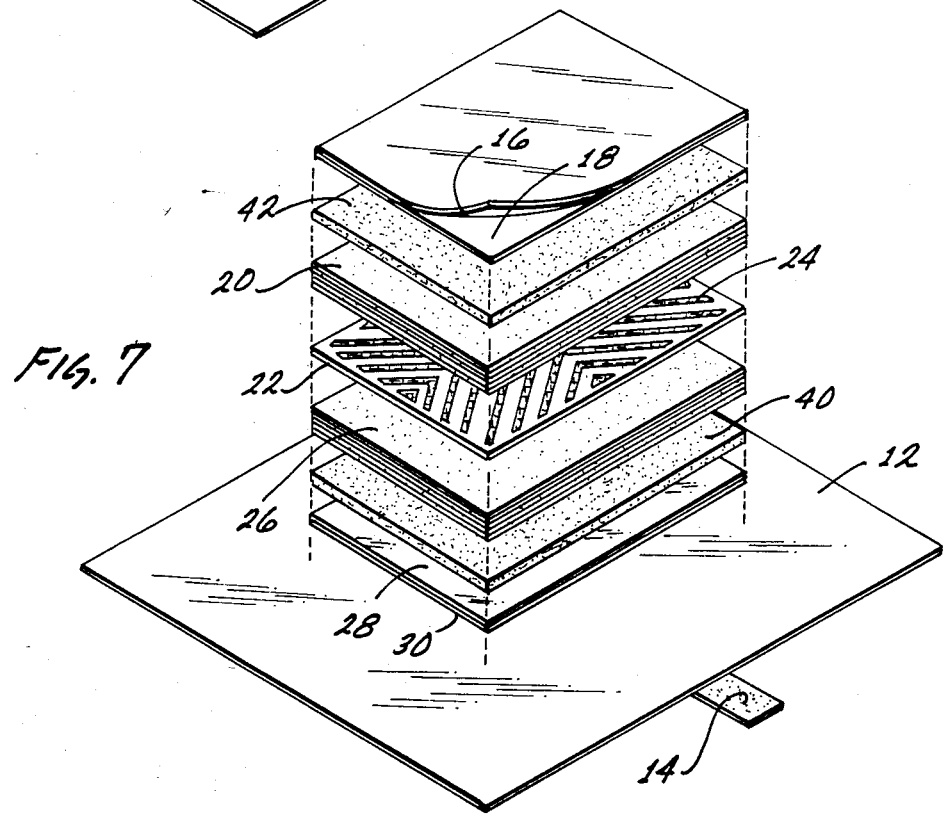
FIG. 7 is an exploded perspective view of the contents of the vacuum test pack incorporating a plurality of foam layers.

A substrate 18 having a nonporous layer 16 attached thereto by any means well known in the art, such as by lamination, is placed so the porous pad 20 is interposed between the nonporous layer 16 and the indicator sheet 22. A substrate 28 having a nonporous layer 30 attached thereto by any means well known in the art is placed so the porous pad 26 and foam layer 40 are interposed between the nonporous layer 30 and the indicator sheet 22. Preferably, both the nonporous layer 16 and nonporous layer 30 are a nonporous gas impermeable plastic. As indicated in FIGS. 1 and 6, nonporous layers 16 and 30 are plastic laminates. It should be appreciated, however, that any kind of a nonporous material will be sufficient for purposes of the invention. For example, a metal sheet or foil or a layer of index cards could be effective for purposes of nonporous layer 16 and nonporous layer 30. Indeed, within the environment of intended use for the present invention, any material will suffice for the nonporous layer so long as it is relatively nonporous and gas impermeable compared to the porous layers. Such a configuration is shown as an alternate embodiment in FIG. 5. As can be seen in FIGS. 6 and 7 when all layers are placed in contact with each other, the edge portions of porous pad 20, porous pad 26 and foam layer 40 are left exposed to allow for evacuation of air from around indicator sheet 22 in a partial vacuum. Also, nonporous material (not shown) can be placed over parts of the edge portions of porous pads 20 and 26 to further reduce the amount of exposed surface.

The exposed surfaces on porous pad 20 and porous pad 26 permit the subsequent introduction of steam to sensitize the indicator ink 24 imprinted on indicator sheet 22 for the purpose of showing the effectiveness of the vacuum. It should be recognized that in the preferred embodiment the nonporous layers 16 and 30 block the passage of air through the top and bottom surfaces of the pack and redirect the air through the edges to inhibit evacuation of air from the porous pads 20 and 26. Thus, with the use of such nonporous layers, the porous pads 20 and 26 can be reduced in size and still provide for an efficacious test of the partial vacuum. This, consequently, allows for a much more compact test pack 10.

As can be appreciated by cross referencing FIG. 6 and FIG. 2, the combination of indicator sheet 22, porous pad 20, porous pad 26, foam layer 40 and the nonporous layer 16 and nonporous layer 30 are enclosed within a CSR overwrap 12. An autoclave indicator tape 14 can then be used to secure the overwrap 12. Use of an indicator tape 14 imprinted with a steam sensitive indicator ink 32, of a kind well known in the art, has the additional advantage of showing when the entire test pack 10 has been exposed to a steam sterilization process.

To assemble the pack 10, the indicator sheet 22 is placed between a porous pad 20 and a porous pad 26. A foam layer 40 is placed on the side of porous pad 26 opposite indicator sheet 22. This combination of pads and foam layer is then interposed between a nonporous layer 16 and a nonporous layer 30. The entire combination is wrapped within a CSR overwrap 12 which is held in place by the autoclave indicator tape 14 to form the test pack 10. The efficiency of an autoclave vacuum system is tested by placing the pack 10 into the coolest area of an autoclave chamber as shown schematically in FIG. 3. Generally, the coolest area is in the front of the autoclave chamber 36 on its floor near the door (not shown). Though there are several acceptable procedures, in a typical test procedure the pack 10 is first placed in this location in the autoclave chamber 36 and a vacuum is then drawn. Steam is then admitted into the autoclave chamber 36 for approximately 3½ minutes. If the vacuum has been ineffective, introduction of the steam will cause any air entrapped within the pack 10 to form as a bubble approximately near the center of the pack 10. The presence of this bubble (not shown) stops further penetration of the steam and thus insulates whatever is within the bubble from the sterilizing effect of the steam. This also prevents the steam from interacting with the indicator ink 24 in the vicinity of the bubble (not shown). The vacuum test pack 10 can then be withdrawn from the autoclave chamber 36 and the indicator sheet examined to determine whether the indicator ink 24 has changed color and if so, to what extent it has changed color. Any failure of the indicator ink 24 to change color indicates the presence of air within the test pack 10 which was not evacuated during the drawing of the vacuum. The presence of air in turn indicates an inefficiency of the vacuum system. It follows that an inefficient vacuum will not provide the proper conditions for an acceptable sterilization process.

In addition to inefficiency of the vacuum system on the autoclave, there are other types of failures which will cause the indicator ink 24 to make an incomplete or only partial color change. For example, a timing error in the duration of the test, insufficient steam temperature, and incomplete injection of steam into the autoclave chamber 36 are all factors which could result in only a partial color change for indicator ink 24. However, unlike vacuum inefficiency, such failures generally show a uniform color change of indicator ink 24. As described above, vacuum inefficiency manifests itself as a color change discontinuity of the indicator ink 24 caused by the presence of an air bubble.

In an alternate embodiment of the present invention shown in FIG. 7, an additional foam layer 42 is placed in the test pack between porous pad 20 and nonporous layer 16. In all important particulars, both as to structure and function, foam layer 42 is equivalent to foam layer 40. It will also be understood by those skilled in the relevant art that foam layer 40 and foam layer 42 may be respectively embedded within porous pad 20 and porous pad 26 without departing from the spirit of the present invention.

While the particular test pack as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A method for constructing a disposable sterilizer vacuum test pack comprising the steps of:
    a. stacking a plurality of selectively porous layers to create a bundle having a top surface and a bottom surface and an edge therebetween;
    b. interposing a sheet with a steam sensitive indicator ink printed thereon between layers of said bundle;
    c. positioning a foam layer against said top surface of said bundle to substantially align its edge with the edge of said bundle to permit the circulation of gas over said top surface;
    d. positioning a first nonporous gas impermeable layer against said foam layer opposite said bundle to direct the passage of air through the edge of said foam layer;
    e. positioning a second nonporous gas impermeable layer against said bottom surface of said bundle to block the passage of air therethrough and aligning said second layer to sufficiently expose the edges of said bundle and said foam layer for evacuation of air therefrom in a preselected partial vacuum and to permit subsequent replacement thereof with steam for exposure of the indicator ink on said sheet to indicate the efficiency of the sterilizer; and
    f. folding a porous overwrap around the combination of said bundle, said indicator sheet, said foam layer and said first and second nonporous layers to maintain the integrity thereof.

2. A disposable pack for testing the efficiency of a steam sterilizer apparatus to create a vacuum which comprises:
    a selectively porous bundle constructed of a plurality of selectively porous layers wherein said bundle has a top surface and a bottom surface with an edge therebetween;
    a sheet with a steam sensitive indicator ink printed thereon interposed between layers of said bundle;
    a first foam layer positioned against said top surface of said bundle having an edge substantially aligned with the edge of said bundle to permit circulation of gas over said top surface;
    a first nonporous gas impermeable layer positioned against said foam layer opposite said bundle to direct the passage of air through the edge of said foam layer; and
    a second nonporous gas impermeable layer positioned against said bottom surface of said handle to block the passage of air therethrough and aligned to leave sufficient exposure at the edges of said bundle and said foam layer for evacuation of air therefrom in a preselected partial vacuum and to permit subsequent replacement thereof with steam for exposure of the indicator ink on said sheet to indicate the efficiency of the sterilizer.

3. A pack as cited in claim 2 wherein said porous bundle comprises a plurality of sheets of blotter paper.

4. A pack as cited in claim 3 further comprising:
    a porous overwrap folded around said bundle, said foam layer, said first nonporous layer and said second nonporous layer to maintain the integrity thereof.

5. A pack as cited in claim 4 wherein said first nonporous layer is a metal foil and said second nonporous layer is a metal foil.

6. A pack as cited in claim 4 further comprising:
a tape for holding said overwrap in place and having an indicator ink printed thereon to show when said pack has been exposed to a steam sterilizing medium.

7. A pack as cited in claim 6 further comprising a second foam layer interposed between the bottom surface of said bundle and said second nonporous layer and having an edge substantially aligned with the edge of said bundle to form an extension thereof to permit circulation of gas over the bottom surface.

8. A pack as cited in claim 7 wherein said first nonporous layer is a gas impermeable plastic laminate and said second nonporous layer is a gas impermeable plastic laminate.

* * * * *